United States Patent [19]

Lamont

[11] Patent Number: Plant 7,545

[45] Date of Patent: Jun. 4, 1991

[54] *LESCHENAULTIA FORMOSA* VARIETY 'FLAMINGO'

[75] Inventor: Gregory P. Lamont, Wyoming, Australia

[73] Assignee: Ornamental Native Australian Plants Pty Ltd, Armidale, Australia

[21] Appl. No.: 427,593

[22] Filed: Oct. 27, 1989

[30] Foreign Application Priority Data

Oct. 31, 1988 [AU] Australia ..... 88/034

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Ernest M. Anderson

[57] ABSTRACT

A new and distinct variety of *Leschenaultia formosa* characterized by the combination of a large flower with frilled and rounded lower wings, deep pink petals and a bushy and erect growth habit.

1 Drawing Sheet

ORIGIN OF THE VARIETY

This variety arises from the controlled pollination in July 1986 at the Horticultural Research Station, Gosford New South Wales Australia, of a commercial variety of *L. formosa* "Princess Pink" by a collected *L. formosa* plant with small orange/red flowers, Breeders Accession No. 5. Seeds were germinated and a seedling was selected for its growth habit, flowering duration and the size and color of its flowers. Subsequent plants have been propagated asexually from that seedling by tissue culture and stem cuttings. The subsequent plants produced possess all the characteristics or come true to form with the original plant and the characteristic features are firmly fixed and maintained in the succeeding generations of plants.

SUMMARY OF THE VARIETY

"Flamingo" is a small bushy erect herbaceous perennial plant 10.0–17.0 cm tall. The foliage is dense with small green fleshy leaves crowding the stems. The flowering season of "Flamingo" is from April to October in the southern hemisphere. Flowering occurs in a cyclical and frequent pattern throughout the year in protected cultivation. The fan shaped flowers are large, mean 25.1 mm wide and means 19.8 mm high, and deep pink in colour. The lower wings of the flower are frilled and rounded. "Flamingo" is a fertile plant and is suitable as a potted flowering ornamental.

DESCRIPTION OF THE PHOTOGRAPHS

The accompanying photographs show typically:

(i) the plant form and size and the display of flowers;
(ii) the size and color of the perianth of "Flamingo" (left) relative to "Princess Pink".

The colors are as nearly true as reasonably possible in colour representations of this type.

DESCRIPTION OF THE VARIETY

In the following botanical description color references are made to The Royal Horticultural Society Colour Chart. Descriptions are based on observations made during August 1988 of 20 randomly selected, 12 month old well-fertilized potted plants growing in open sided unheated polyethylene greenhouses at the Horticultural Research Station, Gosford New South Wales Australia.

Name: "Flamingo".
Botanical name: *Leschenaultia formosa* Goodeniaceae.
Commercial use: Potted flowering ornamental plant.
Form: Small, erect and bushy plant.
Plant characteristics:

- *Height at 4–12 months.*—10–17 cm.
- *Growth habit.*—Erect.
- *Life cycle.*—Herbaceous perennial.
- *Foliage.*—Dense.
- *Stem colour.*—144B green.
- *Leaf.*—Length: Mean 9.56 mm; Range 7.3–12.9 mm. Width: Mean 1.26 mm; Range 0.9–1.7 mm. Color: 136A green.
- *Flowering season.*—Cyclical and frequent through the year.
- *Flower.*—Width: Mean 25.1 mm; Range 21.9–27.4 mm. Height: Mean 19.8 mm; Range 18.1–21.4 mm.
- *Corolla length from base to petal slit.*—Mean 13.0 mm; Range 10.7–14.2 mm.
- *Ovary length.*—Mean 11.23 mm; Range 9.0–13.0 mm.
- *Lower wing width.*—Mean 5.23 mm; Range 4.2–6.1 mm.
- *Slit at bottom of lower petal.*—Narrow.
- *Petal color.*—Deep pink. Just open: 48B whole. Fully open: 61B margin, 61C body. Aged: 61C margin, 63B body, 31C center.
- *Corolla tube main color (external).*—59D dark pink.

COMPARISONS WITH OTHER KNOWN SIMILAR VARIETIES OF LESCHENAULTIA

The seed parent of *L. formosa* "Princess Pink" is an acknowledged variety of the New South Wales nursery trade and is the nearest commercially know available variety.

The observations for the comparison were made under the same circumstances as those for the Description of the Variety.

"Flamingo" has an erect and bushy growth habit compared with the spreading prostrate habit of "Princess Pink".

"Flamingo" has a fully opened flower colour of 61B red/purple margin and 61C red/purple body while "Princess Pink" has a 63A red/purple margin and 49B and C body.

"Flamingo" has a corrola tube mean 13.0 mm long compared with mean 9.7 mm for "Princess Pink".

"Flamingo" has a lower wing width of mean 5.23 mm while "Princess Pink" has a width of mean 3.05 mm.

"Flamingo" has a flower mean 25.1 mm wide and mean 19.8 mm high while "Princess Pink" is mean 17.8 mm wide and mean 13.5 mm high.

"Flamingo" has a flower with a narrow slit at the bottom of the lower petal compared with a pronounced V-shaped notch for "Princess Pink".

The new variety is easy to propagate using either stem cuttings or tissue culture methods. Hardening off of rooted plants takes 2–3 weeks. Production of a flowering pot takes 16–18 weeks.

I claim the following:

1. A new and distinct variety of *Leschenaultia formosa* plant characterized by the combination of a large flower with frilled and rounded lower wings, deep pink petals and a bushy and erect growth habit.

* * * * *

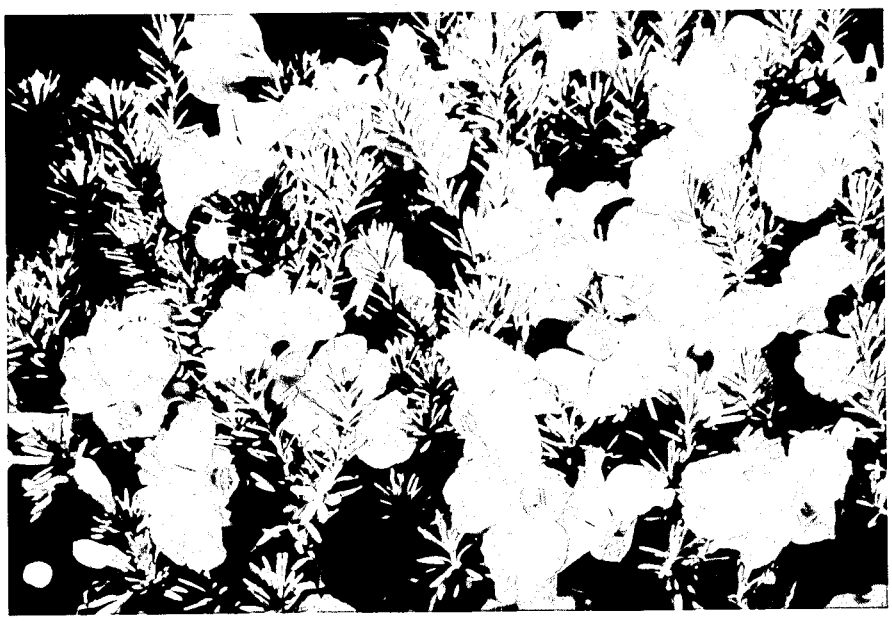
i)
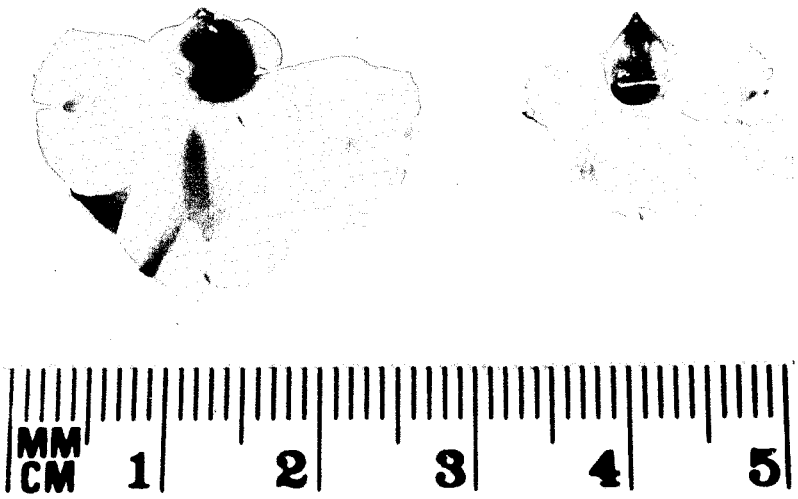
ii)